(12) United States Patent
Wu et al.

(10) Patent No.: US 10,383,885 B2
(45) Date of Patent: Aug. 20, 2019

(54) METHOD FOR TREATING OR PREVENTING DRY EYES

(71) Applicant: Rong-Tsun Wu, Taipei (TW)

(72) Inventors: Rong-Tsun Wu, Taipei (TW); Lin-Yea Horng, New Taipei (TW)

(73) Assignee: Rong-Tsun Wu, Taipei (TW)

( * ) Notice: Subject to any disclaimer, the term of this patent is extended or adjusted under 35 U.S.C. 154(b) by 0 days.

(21) Appl. No.: 15/737,072

(22) PCT Filed: Jun. 16, 2016

(86) PCT No.: PCT/CN2016/000309
§ 371 (c)(1),
(2) Date: Dec. 15, 2017

(87) PCT Pub. No.: WO2016/201953
PCT Pub. Date: Dec. 22, 2016

(65) Prior Publication Data
US 2018/0193369 A1   Jul. 12, 2018

Related U.S. Application Data

(60) Provisional application No. 62/180,450, filed on Jun. 16, 2015.

(51) Int. Cl.
*A61K 31/7034* (2006.01)
*A61K 9/00* (2006.01)
*A61P 27/04* (2006.01)

(52) U.S. Cl.
CPC ........ *A61K 31/7034* (2013.01); *A61K 9/0048* (2013.01); *A61P 27/04* (2018.01)

(58) Field of Classification Search
CPC .... A61K 31/7034; A61K 9/0048; A61P 27/04
USPC ........................................ 514/544
See application file for complete search history.

(56) References Cited

U.S. PATENT DOCUMENTS

| 6,468,998 | B1 | 10/2002 | Kuroita et al. |
| 6,624,193 | B1 | 9/2003 | Naka et al. |
| 2006/0292099 | A1* | 12/2006 | Milburn ............... A61K 9/0019 424/70.1 |
| 2010/0160243 | A1 | 6/2010 | Wu |
| 2012/0164242 | A1* | 6/2012 | Yu ...................... A61K 31/7034 424/725 |

FOREIGN PATENT DOCUMENTS

| CN | 1387436 A | 12/2002 |
| CN | 1539844 A | 10/2004 |
| CN | 101966193 A | 2/2011 |
| CN | 102316873 A | 1/2012 |
| CN | 103524576 A | 1/2014 |
| WO | WO 00/26186 A1 | 5/2000 |

OTHER PUBLICATIONS

International Search Report, issued in PCT/CN2016/000309, dated Sep. 14, 2016.
Written Opinion of the International Searching Authority, issued in PCT/CN2016/000309, dated Sep. 14, 2016.

* cited by examiner

*Primary Examiner* — Yih-Horng Shiao
(74) *Attorney, Agent, or Firm* — Birch, Stewart, Kolasch & Birch, LLP

(57) ABSTRACT

A method for treating or preventing dry eyes is disclosed. The method comprising administering a compound to a subject in need thereof, wherein the compound is a 2,3,5,4'-tetrahydroxystilbene 2-O-β-D-glucopyranoside represented by the general formula (I) below, wherein R is a glucose.

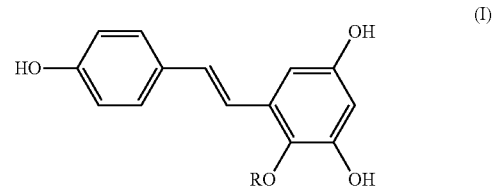

2 Claims, 2 Drawing Sheets

METHOD FOR TREATING OR PREVENTING DRY EYES

CROSS REFERENCE TO RELATED APPLICATIONS

This application is the National Phase of PCT International Application No. PCT/CN2016/000309, filed on Jun. 16, 2016, which claims priority under 35 U.S.C. 119(e) to U.S. Provisional Application No. 62/180,450, filed on Jun. 16, 2015, all of which are hereby expressly incorporated by reference into the present application.

FIELD OF THE INVENTION

The present invention relates to the treatment and prevention of dry eyes with a compound, which is a 2,3,5,4'-tetrahydroxystilbene 2-O-β-D-glucopyranoside.

BACKGROUND OF THE INVENTION

Dry eye syndrome is generally known as keratoconjunctivitis sicca. Millions of people are suffering from this common eye disorders every year. There are many factors that can influence the risk of dry eye syndrome. The rapid development of electronic products is the most common reason for causing dry eye syndrome nowadays. With the rise in smart phones, tablet, laptop, etc. comes a strong increase in the number of dry eye disease patients. Therefore, to develop a treatment and prevention method for dry eye syndrome is an important research topic.

American Academy of Ophthalmology announced the definition of dry eye disease is that normal tear film has one of the following disorders: (1) decreased tear production or (2) excessive tear evaporation, an abnormality in the production of mucus or lipids normally found in the tear layer. Dry eye syndrome can also be divided into different levels base on the symptoms and severity. The symptoms of dry eye include dry, sleepy, itching, irritated eyes, excessively watery eyes, burning and stinging, a foreign body sensation, light sensation, and blurred vision. When the symptoms are severed, the patient's eye will be swollen, congestion and even cause vision damage, etc.

Substantiation risk factors of developing dry eye include aging, deficiency of male hormone secretion in postmenopausal women, lack of nutrients, alcoholism, corneal damage caused by infection or chemical burn, exophthalmoses of hyperthyroidism, facial or trigeminal nerve palsy, long-term contact lens wear and autoimmune diseases such as Sjögren's syndrome, systemic lupus erythematosus, erythemamultiforme and rheumatoid arthritis, etc.

Regular treatments for dry eye syndrome include artificial tears, surgical operation to remove punctual plugs and corticosteroid drops. In addition, the 0.05% cyclosporine is approved by FDA in 2003 to treat inflammation and androgen deficiency induced dry eye syndrome. Although these treatments can keep eyes moist, prevent tear evaporation and help with dryness of ocular surface, often used of these medications might increase not only the risk of the toxic and irritation effects but also give rise to drug resistant infections. As a consequence, non-steroidal anti-inflammatory drugs (NSAID) are increasingly used as dry eye treatment instead of steroids.

Nerve growth factor (NGF) was discovered in the 1950s, which is important for the growth, maintenance, and survival of certain target neurons (nerve cells). It also functions as a signaling molecule. There are two receptors Trk A and p75NTR. NGF and its receptors are also proven to be expressed by the rat lacrimal gland tissue, and also been quantified in human tears (Lee, H. K., et al., Am J Ophthalmol, 2005. 139(6): p. 965-71). Moreover, NGF has been shown to induce in vitro corneal epithelial cell proliferation and differentiation and in the tear film and corneal epithelium, which play an important role in ocular surface maintenance and corneal wound healing (Lambiase, A., et al., Invest Ophthalmol Vis Sci, 2009. 50(10): p. 4622-30). The NGF eye drops were found in the dog's dry eye model can increase tear secretion and conjunctival goblet cell density (Coassin, M., et al., Graefes Arch Clin Exp Ophthalmol, 2005. 243(2): p. 151-5). In clinical, the dry eye patients increased the NGF expression in tears, which is a compensatory mechanism of dry eye patients to maintain the normal function of the ocular surface (Lambiase, A., et al., Arch Ophthalmol, 2011. 129(8): p. 981-6). In addition, NGF can induce the conjunctival epithelial cells differentiate into goblet cell which has the ability to secrete mucin to protect the ocular surface (Lambiase, A., et al., Invest Ophthalmol Vis Sci, 2009. 50(10): p. 4622-30; and Lambiase, A., et al., Proc Natl Acad Sci USA, 2009. 106(32): p. 13469-74). However, these results show that regulation of NGF is a key factor of the treatment of dry eye and eye protection.

There remains a need for a safer and more effective treatment for dry eyes.

BRIEF SUMMARY OF THE INVENTION

The invention provides a method for treating or preventing dry eyes, comprising administering an effective amount of a compound having a general Formula (I) to a subject in need thereof

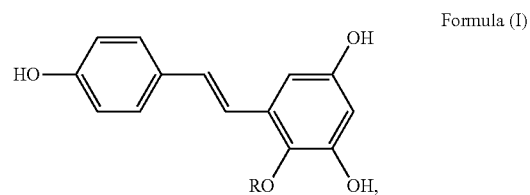

Formula (I)

wherein R is a glucose.

In certain embodiments of the present invention, the compound of Formula (I) is administered in an amount effective to increase tear secretion of the subject.

In certain embodiments of the present invention, the compound of Formula (I) is administered in an amount effective to increase endogenous NGF secretion of the lacrimal tissue in the subject.

It is to be understood that both the foregoing general description and the following detailed description are exemplary and explanatory only and are not restrictive of the invention.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred.

In the drawings.

DETAILED DESCRIPTION OF THE INVENTION

Figure 1:
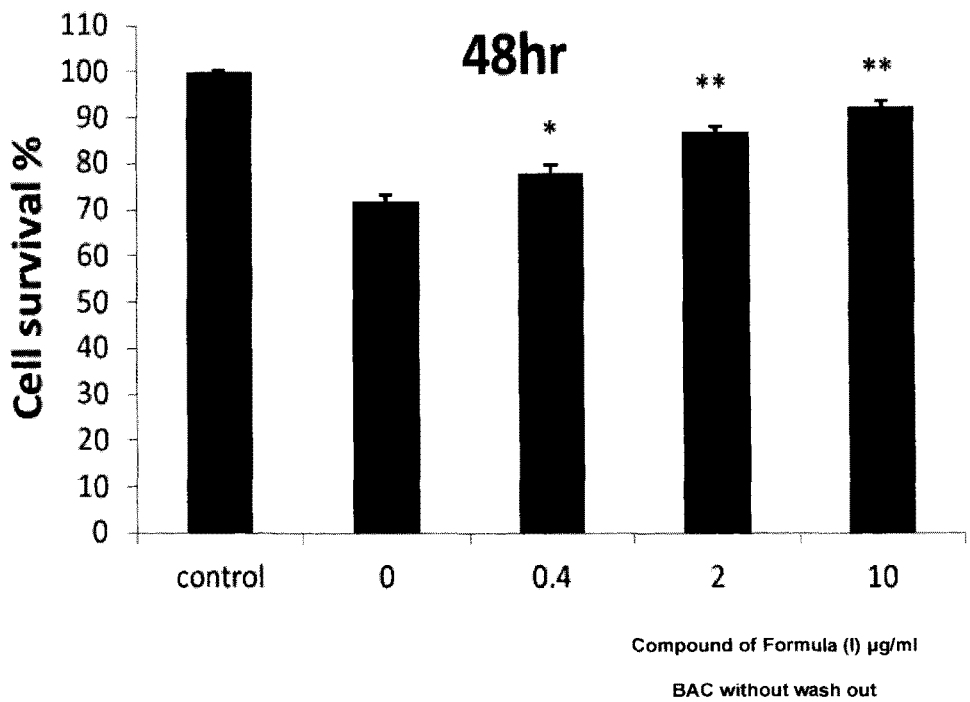
FIG. 1 shows the effect of a compound of Formula (I) on BAC induced damage in HCE cells.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximately, meaning that the term "around", "about" or "approximately" can be inferred if not expressly stated.

In one aspect, the invention provides a method for treating or preventing dry eyes. The method comprises administering an effective amount of a compound having a general Formula (I) to a subject in need thereof.

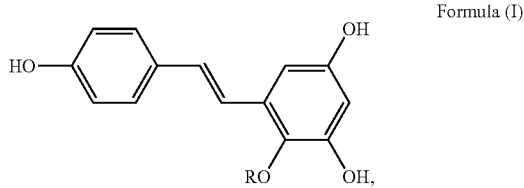

Formula (I)

wherein R is a glucose.

The compound of Formula (I) can be prepared by methods known in the art, for example, those disclosed in US 20100160243 A1, which is hereby incorporated by reference in its entirety.

As used herein, the term "effective amount" refers to a sufficient amount of a compound of Formula (I) to provide desired therapeutic or preventive effects, or the induction of a particular type of response. The effective amount required varies from subject to subject, depending on the disease state, physical conditions, age, sex, species and weight of the subject, etc. However, an appropriate effective amount can be determined by one of ordinary skill in the art using only routine experimentation. In certain embodiments of the present invention, the effective amount is an amount effective to increase tear secretion of a subject. In certain embodiments of the present invention, the effective amount is an amount effective to increase endogenous NGF secretion of the lacrimal tissue (or lacrimal gland) in a subject.

The compound of Formula (I) may be administered to a subject through ophthalmological administration, 1-10 applications at a time, 1-10 times daily, preferably 1-5 applications at a time, 1-4 times daily. For example, one may use 3 drops of a preparation comprising the compound of Formula (I) each time, 3 times daily. For topical ophthalmological administrations, compound of Formula (I) with a concentration of 1-20 µg/ml may be used, preferably, compound of Formula (I) with a concentration of 2-10 µg/ml may be used.

Preferably, the compound of Formula (I) is administered topically to the eyes of the subject.

In another aspect, the present invention provides a topical ophthalmic composition for treating or preventing dry eyes, comprising a compound of Formula (I), and a pharmaceutically acceptable carrier.

The composition of the present invention can be manufactured by conventionally known methods with one or more pharmaceutically acceptable carriers. The term "pharmaceutically acceptable carrier" as used herein encompasses any of the standard pharmaceutical carriers. Such carriers may include, but are not limited to: saline, buffered saline, dextrose, water, glycerol, ethanol, propylene glycol, cremophor, nanoparticles, liposome, polymer, and combinations thereof.

In one further aspect, the present invention provides use of a compound of Formula (I) in the manufacture of a medicament for treating or preventing dry eyes.

The present invention is further illustrated by the following examples, which are provided for the purpose of demonstration rather than limitation.

EXAMPLES

Benzalkonium chloride (BAC) is one of the most commonly used preservative in ophthalmic solutions. But this preservative has been recognized as a potential risk of dry eye syndrome. Therefore, many in vitro and in vivo models of dry eye syndromes are successfully developed by BAC.

Based on these models we have strongly experimental evidence to prove that a compound of Formula (I) is an effective ophthalmic drugs for dry eye syndromes. First we used benzalkonium chloride to damage human corneal epithelium cells then treat with the compound of Formula (I), and we found that the compound of Formula (I) increased cell viability after damaged. In addition, we used benzalkonium chloride as dry eye inducing agent in our mice model. After a week of damage, we treated the mice with eyes drops containing compound of Formula (I) 2, 5 or 10 µg/ml three times a day, and found such treatment restored tear secretion and increased the NGF gene expression level. The results show that the compound of Formula (I) can activate NGF in lacrimal gland, and increase tear secretion to repair the damage of ocular surface.

Example 1: Effect of Compound of Formula (I) on BAC Induced Damage in HCE Cells

Benzalkonium Chloride Cell Damage Model

The Human Corneal Epithelial (HCE) cells were seeded on a 6-well plate $5 \times 10^5$ cells with 10% FCS in DMEM/F12 for 24 hours. After cell attachment, medium was removed and changed into 0.0005% Benzalkonium chloride for 24 hours, then washed with PBS and treat with different concentrations 0.4, 2, 10 μg/ml of compound of Formula (I) (compound A) for 48 hours. At the end the cells were trypsinized and centrifuge 1000 rpm for 5 minutes, the supernatant was removed, added 1 ml of DMEM/F12 medium to resuspend the cells, followed by 0.4% trypan blue and the cell culture medium were 1:3 dilution, the number of cells were calculate under a microscope to observe the survivability of different concentrations treatment. The results are shown in FIG. 1. *P<0.05, **P<0.01 compared to the 0 μg/ml compound A group, Student's t-test. Data are expressed as mean±SD (n=3).

Example 2: Compound of Formula (I) Improves Tear Secretion in BAC Induced Dry Eye Mice Benzalkonium Chloride Induced Dry Eye Mice Model (1)
Male BALB/c mice (6 weeks) was treated with thrice-daily (9:00, 13:30, 18:00) topical administration of 5 ul of 0.3% BAC in right eyes, mice was treated with PBS as control group, from day 1 to 7. And compound A (2, 5, 10 μg/ml) was treated with thrice-daily (9:00, 13:30, 18:00) topical administration of 5 ul in right eyes, and PBS as control group, from day 8 to 19.

Figure 2:
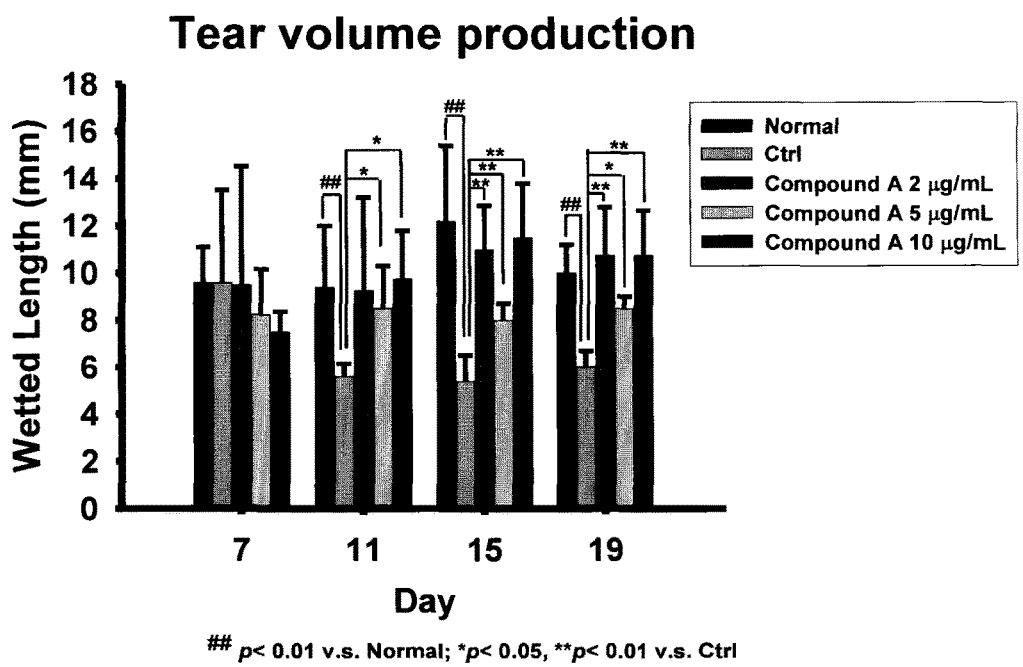
FIG. 2 shows a compound of Formula (I) improves tear secretion in BAC induced dry eye mice model (1).

Phenol red thread tear test was used. The thread is yellow (acidic) and when it comes in contact with tears it changes to a light red color. Forceps were used to insert folded portion of the thread into the palpebral conjunctiva of the eye ⅓ of the distance from the lateral canthus of the lower eye lid. After 15 s, the thread was removed and the entire wet (Red) portion was measured. The phenol red thread test was on 7, 11, 15, 19 day. The results are shown in FIG. 2. *P<0.05, **P<0.01 compared to the control, Student's t-test. Data are expressed as mean±SD (n=5-6).

Benzalkonium Chloride Induced Dry Eye Mice Model (2)
Male BALB/c mice (9 weeks) was treated with thrice-daily (9:00, 13:30, 18:00) topical administration of 5 ul of 0.3% BAC in right eyes, mice was treated with PBS as control group, from day 1 to 7. And compound A (5, 10 μg/ml) was treated with thrice-daily (9:00, 13:30, 18:00) topical administration of 5 ul in right eyes, and PBS as control group, from day 15 to 19.

Figure 3:
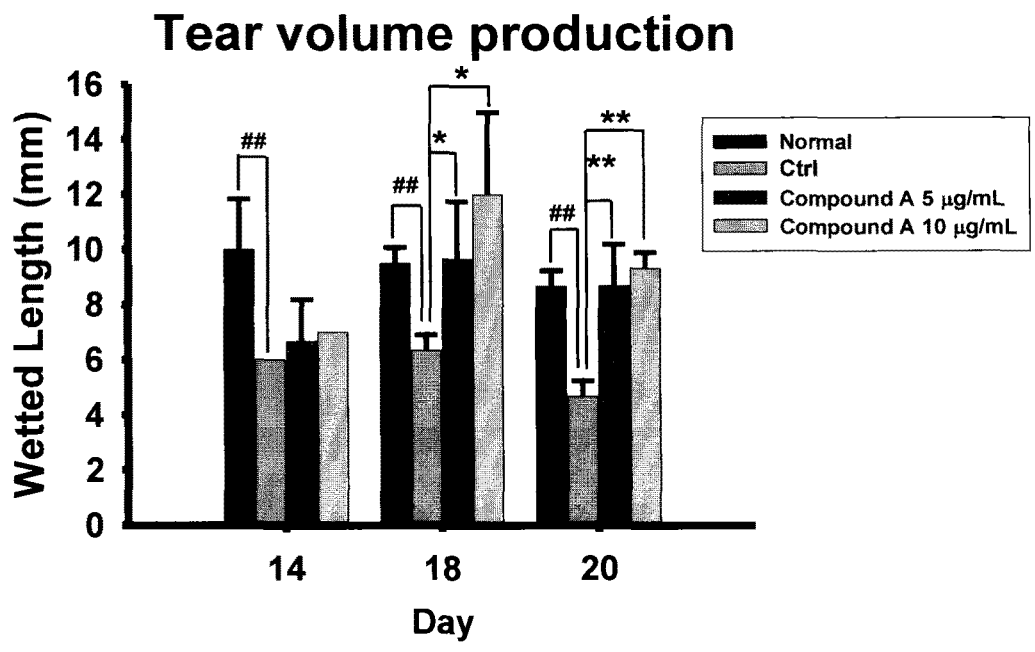
FIG. 3 shows a compound of Formula (I) improves tear secretion in BAC induced dry eye mice model (2).

Phenol red thread tear test was used. The thread is yellow (acidic) and when it comes in contact with tears it changes to a light red color. Forceps were used to insert folded portion of the thread into the palpebral conjunctiva of the eye ⅓ of the distance from the lateral canthus of the lower eye lid. After 15 s, the thread was removed and the entire wet (Red) portion was measured. The phenol red thread test was on 14, 18, 20 day. The results are shown in FIG. 3. *P<0.05, **P<0.01 compared to the control, Student's t-test. Data are expressed as mean±SD (n=5-6).

Example 3: Effect of Compound of Formula (I) on Tear NGF Protein Expression in BAC Induced Dry Eye Mice Tear was collected from right eye of BAC induced dry eye mice by 10 μl PBS wash. Mice treated eyes drop of PBS as control and different concentration Compound A for 10 days. NGF protein was a positive control. 5 μl tear volume used in western blot.

The total protein concentration was determined by 1×Braford assay. To denature, use a loading buffer(7 ml 0.5M Tris pH6.8, 3 ml Glycerol, 1 g 10% SDS, 0.93 g DTT, 0.5 mg 0.05% bromophenol blue, 10 ml), and boil the mixture at 95-100° C. for 5 minutes. Total protein was loaded 20-40 μg per mini-gel (12% SDS-polyacrylamide gel) well for electrophoresis. Then transfer the proteins into polyvinylidene difluoride membrane and blocking the membrane with 5-10% nonfat dried milk in TTBS. The membrane was incubated with the primary antibody overnight at 4° C. by shaking. Wash the membrane several times in TTBS to remove residual primary antibody. And the membrane was incubated with secondary antibody for 2 hours at room temperature.

Figure 4:
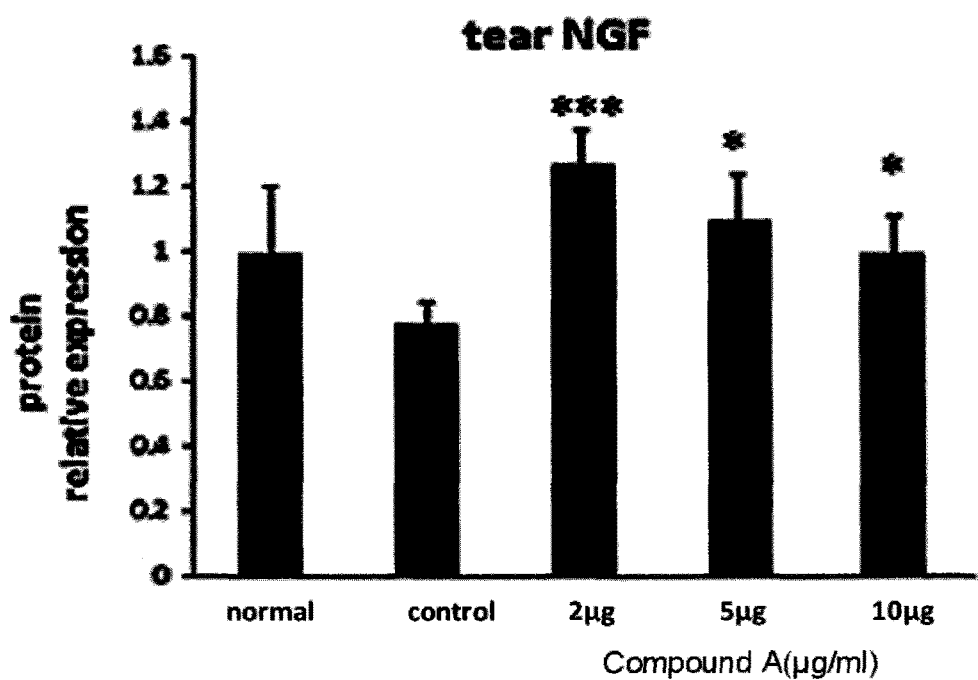
FIG. 4 shows the effect of a compound of Formula (I) on tear NGF protein expression in BAC induced dry eye mice.

The protein levels were determined by chemiluminescene detection system and analysis by Imagequant software. The results are shown in FIG. 4. *P<0.05, P<0.01, *P<0.001 compared to the control, Student's t-test. Data are expressed as mean±SD (n=4).

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:
1. A method for treating or preventing dry eyes comprising
administering a compound having a general Formula (I) to a subject in need thereof

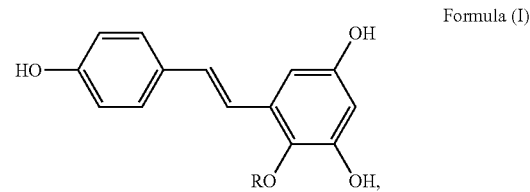

Formula (I)

wherein R is a glucose, and
wherein the compound is administered daily for 12 days or more in an amount effective to increase tear secretion of the subject.
2. The method of claim 1, wherein the compound is administered topically to the eyes of the subject.

* * * * *